US011737779B2

(12) United States Patent
Carlson et al.

(10) Patent No.: US 11,737,779 B2
(45) Date of Patent: Aug. 29, 2023

(54) ATHERECTOMY MOTOR CONTROL SYSTEM

(71) Applicant: BOSTON SCIENTIFIC SCIMED, INC., Maple Grove, MN (US)

(72) Inventors: Corydon Carlson, Stillwater, MN (US); David Gordon Spangler, New Richmond, WI (US); Daniel Frank Massimini, Brooklyn Park, MN (US); Laszlo Trent Farago, Hudson, WI (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 675 days.

(21) Appl. No.: 16/737,567

(22) Filed: Jan. 8, 2020

(65) Prior Publication Data

US 2020/0214735 A1 Jul. 9, 2020

Related U.S. Application Data

(60) Provisional application No. 62/790,316, filed on Jan. 9, 2019.

(51) Int. Cl.
*A61B 17/3207* (2006.01)
*A61B 17/3203* (2006.01)

(52) U.S. Cl.
CPC ........ *A61B 17/320758* (2013.01); *A61B 17/32037* (2013.01)

(58) Field of Classification Search
CPC ...... A61B 17/320758; A61B 17/32037; A61B 17/3207; A61B 17/320725; A61B 2017/00017; A61B 2017/00075; A61B 2017/00022; A61B 2090/066; A61B 2090/08021; G05B 13/0245; G05B 11/42
See application file for complete search history.

(56) References Cited

U.S. PATENT DOCUMENTS 5,766,192 A * 6/1998 Zacca .................... A61F 2/958
606/198
2002/0058956 A1 5/2002 Honeycutt et al.
2006/0074442 A1 4/2006 Noriega et al.
(Continued)

FOREIGN PATENT DOCUMENTS

EP 3053534 A1 8/2016
JP 2002538927 A 11/2002
(Continued)

OTHER PUBLICATIONS

International Search Report and Written Opinion dated Jun. 25, 2020 for International Application No. PCT/US2020/012767.

*Primary Examiner* — Jocelin C Tanner
(74) *Attorney, Agent, or Firm* — Seager, Tufte & Wickhem LLP (57) ABSTRACT

An atherectomy system includes a drive mechanism that is adapted to rotatably actuate an atherectomy burr and a controller that is adapted to regulate operation of the drive mechanism. In some cases, the drive mechanism includes a drive cable that is coupled with the atherectomy burr and an electric drive motor that is adapted to rotate the drive cable. The controller is adapted to regulate operation of the electric drive motor such that the drive mechanism emulates one or more performance parameters of an air turbine.

17 Claims, 12 Drawing Sheets

(56) References Cited

U.S. PATENT DOCUMENTS

| | | | |
|---|---|---|---|
| 2006/0212737 A1* | 9/2006 | Chandra | H02M 7/53871 713/340 |
| 2008/0146965 A1* | 6/2008 | Privitera | A61B 10/0283 600/568 |
| 2010/0125276 A1* | 5/2010 | Palermo | A61B 17/320758 408/1 R |
| 2012/0136348 A1* | 5/2012 | Condie | A61B 18/14 606/34 |
| 2013/0079763 A1* | 3/2013 | Heckel | A61B 18/1206 606/34 |
| 2013/0103062 A1 | 4/2013 | To et al. | |
| 2014/0277014 A1* | 9/2014 | Higgins | A61B 17/320758 606/159 |
| 2015/0025538 A1* | 1/2015 | Kust | B25B 23/147 606/104 |

FOREIGN PATENT DOCUMENTS

| | | |
|---|---|---|
| JP | 2005182161 A | 7/2005 |
| JP | 2008514367 A | 5/2008 |
| JP | 2015512702 A | 4/2015 |
| WO | 0056230 A2 | 9/2000 |
| WO | 2019168784 A1 | 9/2019 |

* cited by examiner

ATHERECTOMY MOTOR CONTROL SYSTEM

CROSS-REFERENCE TO RELATED APPLICATIONS

This application claims the benefit of priority under 35 U.S.C. § 119 to U.S. Provisional Application Ser. No. 62/790,316, filed Jan. 9, 2019, the entirety of which is incorporated herein by reference.

TECHNICAL FIELD

The present disclosure pertains to medical devices, and methods for manufacturing and using medical devices. More particularly, the disclosure is directed to devices and methods for removing occlusive material from a body lumen. Further, the disclosure is directed to an atherectomy device for forming a passageway through an occlusion of a body lumen, such as a blood vessel.

BACKGROUND

Many patients suffer from occluded arteries and other blood vessels which restrict blood flow. Occlusions can be partial occlusions that reduce blood flow through the occluded portion of a blood vessel or total occlusions (e.g., chronic total occlusions) that substantially block blood flow through the occluded blood vessel. In some cases a stent may be placed in the area of a treated occlusion. However, restenosis may occur in the stent, further occluding the vessel and restricting blood flow. Revascularization techniques include using a variety of devices to pass through the occlusion to create or enlarge an opening through the occlusion. Atherectomy is one technique in which a catheter having a cutting element thereon is advanced through the occlusion to form or enlarge a pathway through the occlusion. A need remains for alternative atherectomy devices to facilitate crossing an occlusion.

SUMMARY

This disclosure provides design, material, manufacturing method, and use alternatives for medical devices. For example, an atherectomy system may include an electric drive mechanism that is adapted to rotatably actuate an atherectomy burr and a controller that is adapted to regulate operation of the electric drive mechanism such that the electric drive mechanism emulates one or more performance characteristics of an air turbine.

Additionally or alternatively, the one or more performance characteristics of an air turbine may include torque versus speed.

Additionally or alternatively, the electric drive mechanism may include a drive cable that is coupled with the atherectomy burr and an electric drive motor that is adapted to rotate the drive cable.

Additionally or alternatively, the controller may include a reference block that is adapted to receive a speed signal and output a reference signal, a control block that is adapted to receive the reference signal from the reference block and generate a resulting control effort signal and a drive circuit that is adapted to receive the control effort signal from the control block and regulate operation of the drive mechanism accordingly.

Additionally or alternatively, the control block may include a controller that utilizes a P gain, an I gain and a D gain, modified to include a variable K offset value summed with a sum of the P gain, the I gain and the D gain.

Additionally or alternatively, the controller may be configured to set an initial value for the variable K offset value equal to zero.

Additionally or alternatively, the controller may be configured to calculate a new value for the variable K offset value when the electric drive motor reaches a speed reference value.

Additionally or alternatively, the controller may be further configured, when the electric drive motor reaches the speed reference value, to calculate a new value for the P gain.

Additionally or alternatively, the controller is further configured, when the electric drive motor reaches the speed reference value, to calculate a new value for P gain in accordance with equation (1):

$$P_{new} = \frac{T_{stall}(P_{old} + I_{old})}{\omega_{ref}}, \quad (1)$$

where
$P_{new}$ is a new P gain value;
$P_{old}$ is a previous P gain value;
$I_{old}$ is a previous I gain value;
$T_{stall}$ is a desired stall torque value; and
$\omega_{ref}$ is the speed reference value.

Additionally or alternatively, the PID controller may be further configured, when the electric drive motor reaches the speed reference value, to calculate a new value for the variable K term in accordance with equation (2):

$$K = P_{old} + I_{old} \quad (2).$$

Additionally or alternatively, the PID controller may be further configured to calculate new values for the variable K term and the P term in accordance with equations (3) and (4):

$$K = P*e + I*\int e \quad (3)$$

$$P_{new} = \frac{i_{stall} - K}{\omega_{ref}}, \quad (4)$$

where
$i_{stall}$ is the motor current that corresponds to a desired stall torque; and
e is the error or difference between reference speed and the speed.

As another example, an atherectomy system includes a drive mechanism that is adapted to rotatably actuate an atherectomy burr and a control system that is adapted to regulate operation of the drive mechanism. The control system includes a reference block for providing a speed reference value and a controller that is operably coupled to the reference block for receiving the speed reference value, the controller adapted to utilize the speed reference value, a Proportional (P) gain value, an Integral (I) gain value, a Derivative (D) gain value and a K offset value in determining an output signal for the drive mechanism. The controller may be further adapted to initiate actuation of the drive mechanism using an initial value for the I gain value and a value of zero for the K offset value and to reduce the I gain value and calculate a non-zero value for the K offset value once a speed of the drive mechanism reaches the speed reference value.

Additionally or alternatively, the controller may be further adapted to also calculate a new P gain value once the speed of the drive mechanism reaches the speed reference value.

Additionally or alternatively, the new P gain value may be related to a desired stall torque value or to the speed reference value.

Additionally or alternatively, the drive mechanism may include a drive cable that is coupled with the atherectomy burr and an electric drive motor that is adapted to rotate the drive cable.

As another example, an atherectomy system includes an electric drive motor that is adapted to actuate an atherectomy burr and a controller that is adapted to regulate operation of the electric drive motor, the controller adapted to utilize a speed reference value, a Proportional (P) gain value, an Integral (I) gain value, a Derivative (D) gain value and a K offset value in determining an output signal for the electric drive motor.

Additionally or alternatively, the controller may be configured to set an initial value for the variable K offset value equal to zero.

Additionally or alternatively, the controller may be configured to calculate a new value for the variable K offset value when the electric drive motor reaches a speed reference value.

Additionally or alternatively, the controller may be further configured, when the electric drive motor reaches the speed reference value, to calculate a new value for the P gain.

Additionally or alternatively, the controller may be further configured to utilize estimated torque as a feedback value.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

Many patients suffer from occluded arteries, other blood vessels, and/or occluded ducts or other body lumens which may restrict bodily fluid (e.g. blood, bile, etc.) flow. Occlusions can be partial occlusions that reduce blood flow through the occluded portion of a blood vessel or total occlusions (e.g., chronic total occlusions) that substantially block blood flow through the occluded blood vessel. Revascularization techniques include using a variety of devices to pass through the occlusion to create or enlarge an opening through the occlusion. Atherectomy is one technique in which a catheter having a cutting element thereon is advanced through the occlusion to form or enlarge a pathway through the occlusion. Ideally, the cutting element excises the occlusion without damaging the surrounding vessel wall and/or a previously implanted stent where restenosis has occurred. However, in some instances the cutting element may be manipulated and/or advanced such that it contacts the vessel wall and/or the stent. Therefore, it may be desirable to utilize materials and/or design an atherectomy device that can excise an occlusion without damaging the surrounding vessel and/or a previously implanted stent where restenosis has occurred. Additionally, it may be desirable that a cutting element be useful in removing hard occlusive material, such as calcified material, as well as softer occlusive material. The methods and systems disclosed herein may be designed to overcome at least some of the limitations of previous atherectomy devices while effectively excising occlusive material. For example, some of the devices and methods disclosed herein may include cutting elements with unique cutting surface geometries and/or designs.

Figure 1:
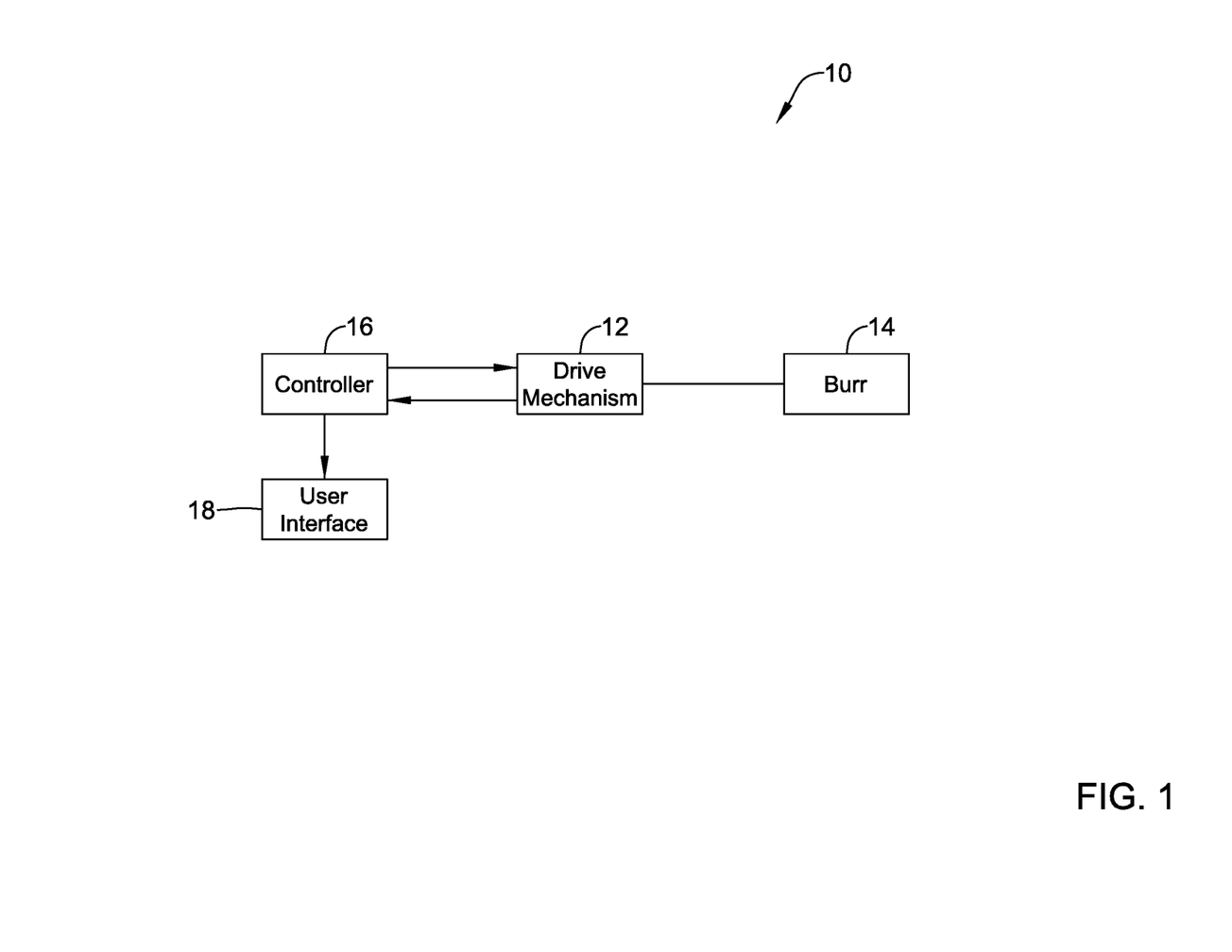
FIG. 1 is a schematic block diagram of an example atherectomy system.

FIG. 1 is a schematic block diagram of an example atherectomy system 10 that includes a drive mechanism 12 that is adapted to rotatably actuate an atherectomy burr 14. The atherectomy system 10 includes a controller 16 that is adapted to regulate operation of the drive mechanism 12. As will be discussed, in some cases the controller 16 regulates operation of the drive mechanism 12 in order to emulate one or more performance parameters of an atherectomy system that is driven by an air turbine, rather than by an electric motor. In some cases, the atherectomy system 10 may include a user interface 18 that may be operably coupled to the controller 16 such that the controller 16 is able to display information regarding the performance of the drive mechanism 12. This information may, for example, include one or more of an instantaneous speed of the drive mechanism 12, an instantaneous torque being experienced by the atherectomy burr 14, and the like. In some instances, the atherectomy system 10 may not include the user interface 18. In some cases, the atherectomy burr 14 may also be referred to as being or including a cutting head or a cutting member, and these terms may be used interchangeably.

Figure 2:
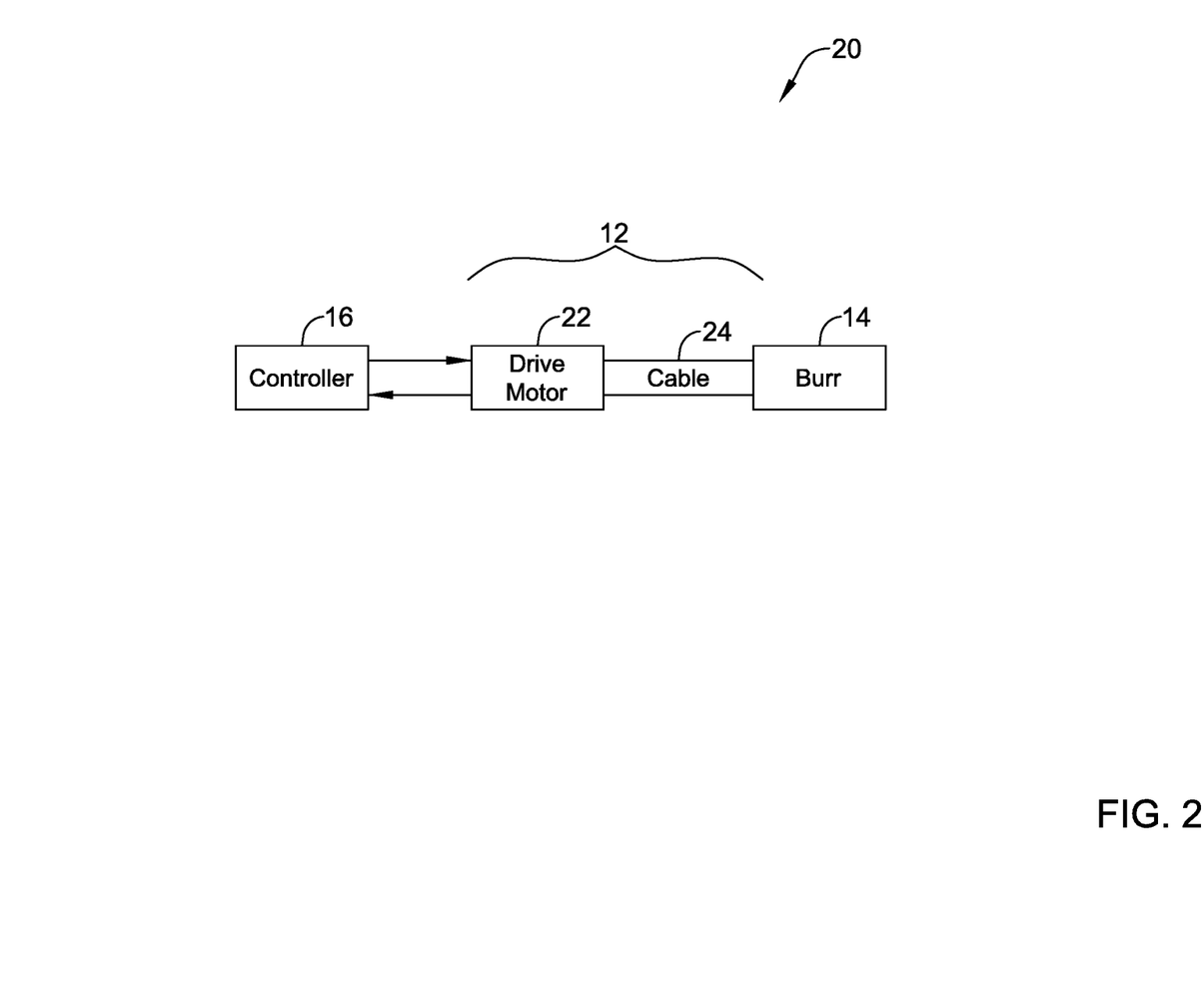
FIG. 2 is a schematic block diagram of an example atherectomy system.

FIG. 2 is a schematic block diagram of an example atherectomy system 20 in which the drive mechanism 12 may include a drive motor 22 and a drive cable 24 that is operably coupled with the drive motor 22 as well as the atherectomy burr 14. In some instances, the drive motor 22 is an electric drive motor. In some cases, features of the atherectomy system 20 may be combined with features of the atherectomy system 10. In some cases, the atherectomy system 20 may also include a handle (not shown).

Figure 3:
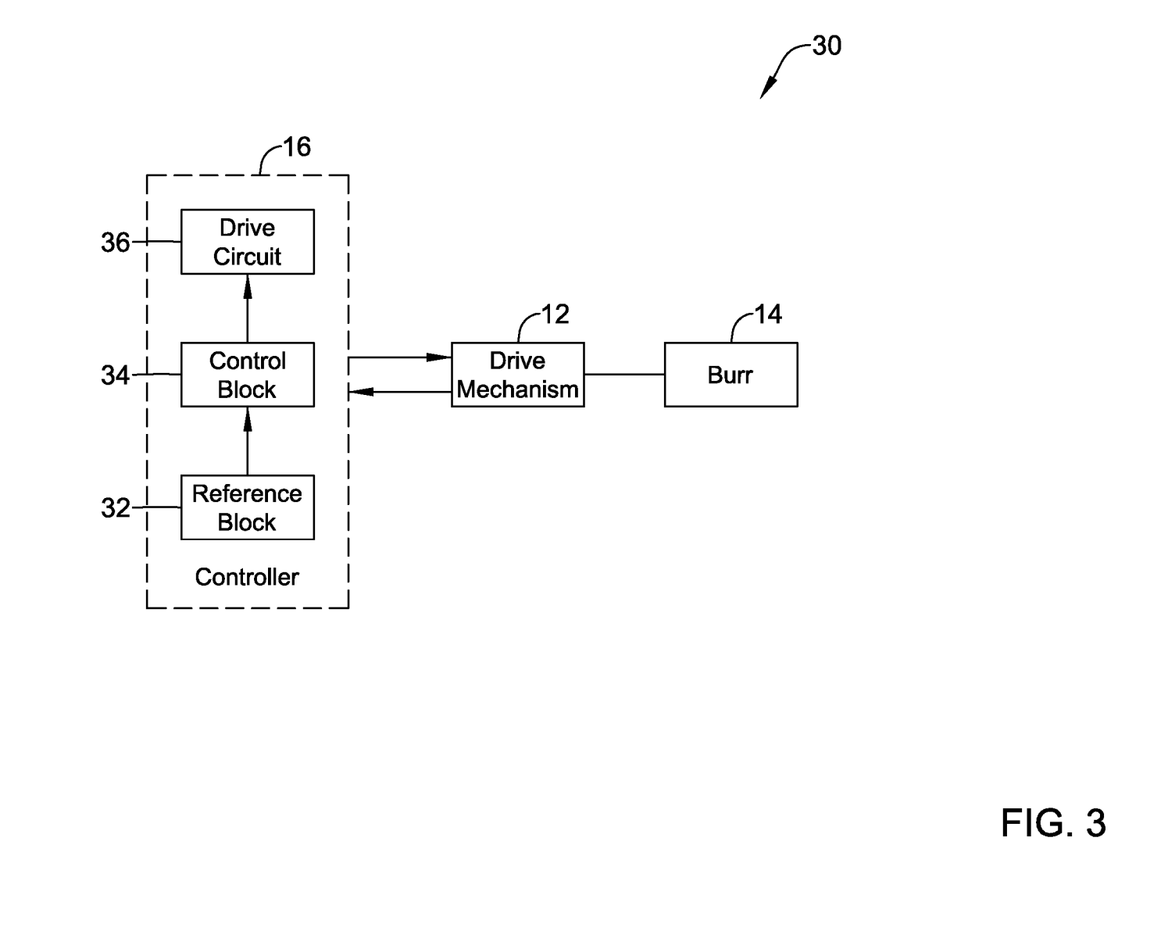
FIG. 3 is a schematic block diagram of an example atherectomy system.

FIG. 3 is a schematic block diagram of an example atherectomy system 30 in which the controller 16 includes a reference block 32, a control block 34 and a drive circuit 36. In some cases, features of the atherectomy system 30 may be combined with features of the atherectomy system 20 and/or the atherectomy system 10. In some cases, the reference block 32 may be adapted to receive a speed signal and to output a reference speed value. The control block 34 may be adapted to receive the reference speed signal from the reference block 32 and to generate a resulting control effort signal. In some cases, the control block 34 includes a P (Proportional) controller. In some instances, the control block 34 includes a Proportional Integral Derivative (PID) controller. In some cases, as will be discussed, the control block 34 may include a PID controller that has been modified to sum a variable K value with the D (Derivative) gain value. The drive circuit 36 may be adapted to receive the control effort signal from the control block 34 and to regulate operation of the drive mechanism 12 accordingly.

Figure 4:
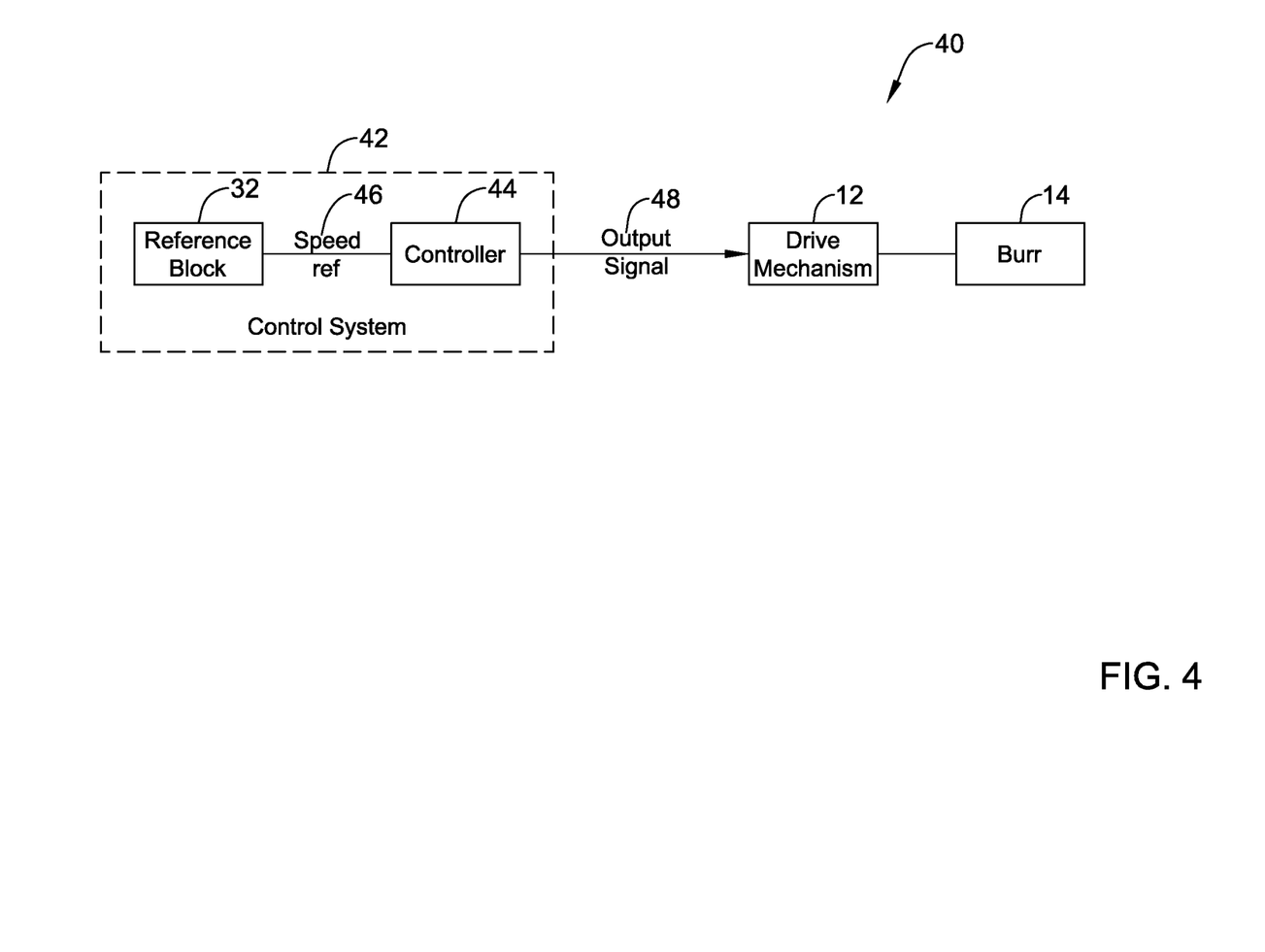
FIG. 4 is a schematic block diagram of an example atherectomy system.

FIG. 4 is a schematic block diagram of an example atherectomy system 40 that includes a control system 42 that is adapted to regulate operation of the drive mechanism 12 in order to rotatably actuate the atherectomy burr 14. In some cases, features of the atherectomy system 40 may be combined with one or more of the atherectomy system 10, the atherectomy system 20 or the atherectomy system 30. The control system 42 may include the reference block 32 as well as a controller 44 that is operably coupled to the reference block 32. In some cases, the reference block 32 may determine a speed reference 46.

In some cases, the controller 44 may be adapted to utilize the speed reference 46, a Proportional (P) gain value, an Integral (I) gain value, a Derivative (D) gain value and a variable K offset value that is summed with the D gain value in determining an output signal 48 for the drive mechanism 12. In some cases, the drive mechanism 12 may include a drive motor and drive cable extending between the drive motor and the atherectomy burr 14. In some cases, the controller 44 may be adapted to regulate operation of the drive mechanism 12 such that the drive mechanism 12 emulates one or more properties of an atherectomy system that is driven by an air turbine, rather than by an electric drive motor. As an example, the torque versus speed properties of an air turbine system may be emulated by the controller 44. In some cases, use of a PID-K controller may be used to introduce a bias that reduces steady state error and to provide a torque basis in cases where system rebound might otherwise be an issue.

Figure 5:
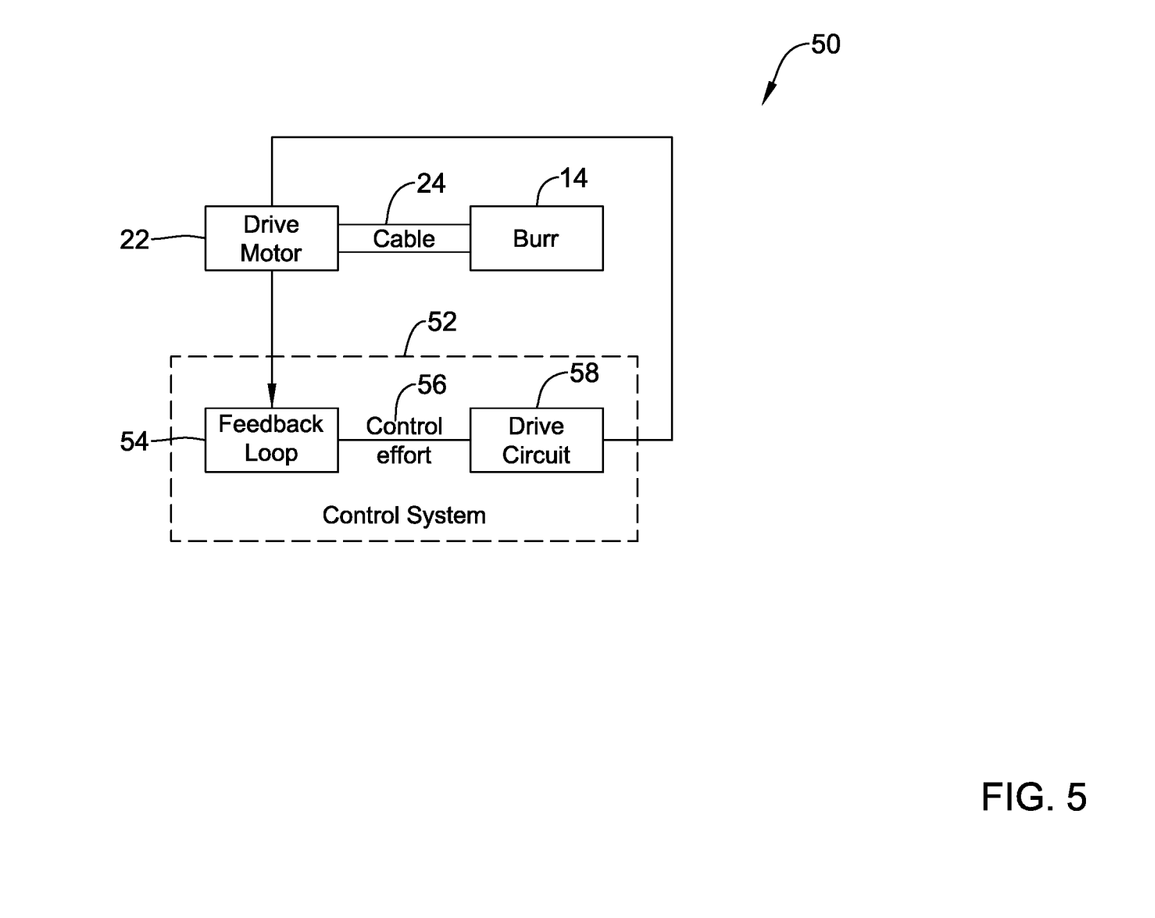
FIG. 5 is a schematic block diagram of an example atherectomy system.

FIG. 5 is a schematic block diagram of an example atherectomy system 50 that includes a control system 52 that is adapted to regulate operation of the drive motor 22 in order to rotatably actuate the atherectomy burr 14. In some cases, features of the atherectomy system 50 may be combined with one or more of the atherectomy system 10, the atherectomy system 20, the atherectomy system 30 or the atherectomy system 40. The control system 52 is operably coupled to the drive motor 22 and includes a feedback loop 54 that is adapted to monitor performance of the drive motor 22 and to output a control effort signal 56. A drive circuit 58 is adapted to receive the control effort signal 56 and to regulate operation of the drive motor 22 in accordance with the control effort signal 56. In some cases, the control system 52 may be further adapted to regulate operation of the drive motor 22 in such a way as to emulate the performance of an air turbine.

In some cases, the feedback loop 54 may include a reference block for determining a speed reference and a controller that is operably coupled to the reference block for receiving the speed reference, the controller adapted to utilize the speed reference, a Proportional (P) gain value, an Integral (I) gain value, a variable K offset value and a Derivative (D) gain value in determining the control effort signal. In some cases, the feedback loop 54 may be adapted to add an offset value to a reference signal provided to the reference loop 54 in order to accurately hold speed of the drive motor 22 during a no-load situation.

Figure 6:
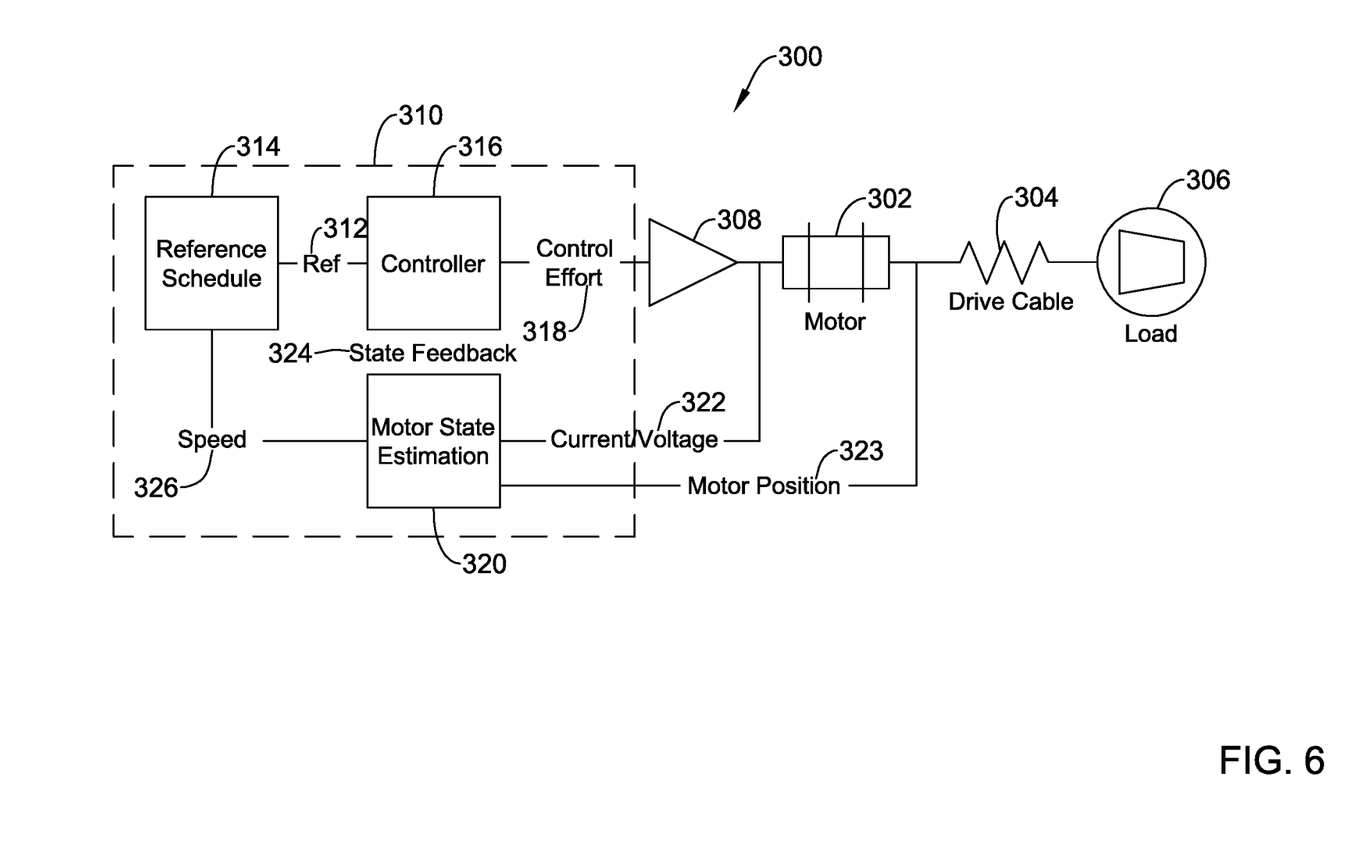
FIG. 6 is a schematic block diagram of an example atherectomy system.

FIG. 6 is a schematic block diagram of an example atherectomy system 300. In some cases, the atherectomy system 300 may be considered as being an example of the atherectomy system 10, 20, 30, 40 or 50. In some instances, features of the atherectomy system 300 may be combined with features of any of the atherectomy systems 10, 20, 30, 40 or 50, for example. The atherectomy system 300 includes a motor 302 that drives a drive cable 304 which itself engages a load 306. The load 306 represents an atherectomy burr, for example. The motor 302 is controlled by a drive circuitry 308 which may be considered as being an example of or otherwise incorporated into the drive module 22 and/or the control system 106, for example.

The drive circuitry 308 receives an input from a feedback portion 310. In some cases, the feedback portion 310 begins with a reference input 312 from a reference schedule block 314, which provides the reference input (or reference error) 312 to a controller 316. In some cases, the reference schedule block 314 may be configured to accept additional inputs, such as from a user and/or from additional sensors not illustrated. As an example, if the device has been running for too long of a period of time, the reference schedule block 314 may reduce the speed reference in order to prevent overheating. A PID controller is a controller that includes a (P) proportional portion, an (I) integral portion and a (D) derivative portion. In some cases, a PID controller may be modified to sum a variable K offset value with the D gain value. The controller 316 outputs a control effort value 318 to the drive circuitry 308. A motor state estimation block 320 receives a current/voltage signal 322 and a motor position signal 323 from the drive circuitry 308 and receives state feedback 324 from the controller 316. The motor state estimation block 320 outputs a speed value 326 back to the reference schedule block 314. While the feedback from the motor state estimation block 320 to the reference schedule block 314 is shown as being a speed value, in some cases the feedback may additionally or alternatively include one or more of position, torque, voltage or current, and in some cases may include the derivative or integral of any of these values. In some cases, the motor state estimation block 320 may instead receive a signal 323 that represents speed, instead of position (as illustrated). The motor position signal 323 may be an indication of relative rotational position of an output shaft of the motor 302, and thus an indication of relative rotational position of the load 306, which if tracked over time may provide an indication of speed.

Figure 7:
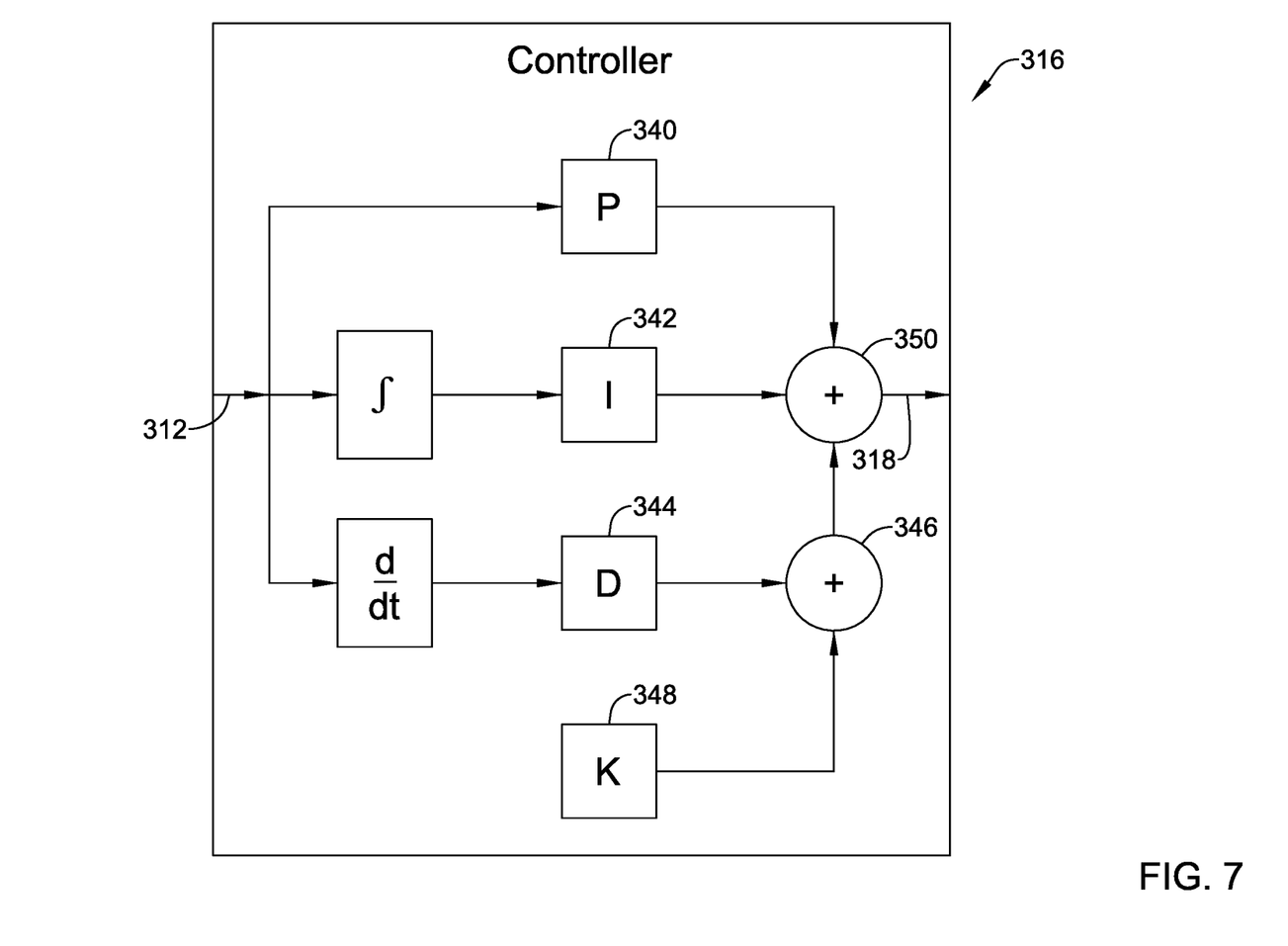
FIG. 7 is a schematic diagram of an example controller usable in the example atherectomy systems of FIGS. 1 through 6.

FIG. 7 is a schematic block diagram of the controller 316, which may be considered as being an example of the controller 44 shown in FIG. 4. A reference signal 312, which is representative of an error between a desired value and an actual value, enters the controller 316. The controller 316 calculates a P value 340, which is proportional to the error. The controller 316 calculates an I value 342, which is an integral with respect to time of the error and a D value 344, which is a derivative with respect to time of the error. The controller 316 calculates a K offset value 348, which is used by the controller 316 in emulating the performance of an air turbine. As illustrated, the D value 344 and the K offset value 348 are added together at a summation point 346, and the resulting value created at the summation point 346 is added together with the P value 340 and the I value 342 at a summation point 350, resulting in an output of the control effort signal 318. In some cases, it will be appreciated that the summation is commutative, meaning that the summation can occur in any desired order.

Figure 8:
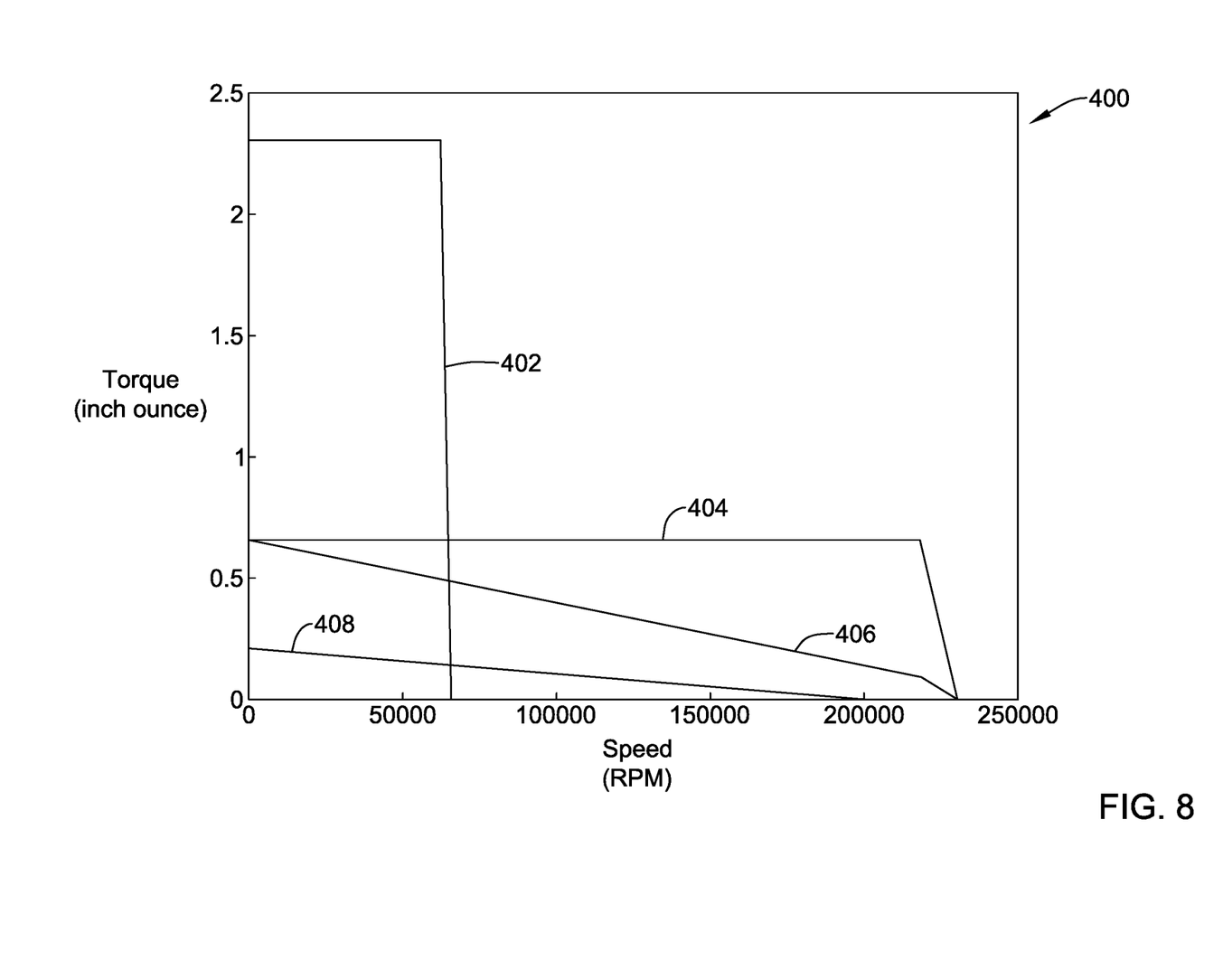
FIGS. 8 through 11 are graphical representations of example torque versus speed curves.

As referenced above, atherectomy systems have previously been driven by air turbines. In some cases, it may be desirable to emulate the performance of an air turbine-driven atherectomy system. For example, there may be a desire to emulate the torque versus speed curve of an air turbine, as some users may expect and/or be accustomed to this. It will be appreciated that the torque versus speed curve of an electric motor is quite different from that of an air turbine. FIG. 8 is a representative plot 400 that shows several torque versus speed curves. Curve 402 represents the torque versus speed curve for an electric motor without any gearing. Curve 404 represents the torque versus speed curve for an electric motor that is geared at 3.5:1. Curve 406 represents the working torque for an electric motor, including system frictional losses. Curve 408 represents the working torque for an air turbine. These curves 402, 404, 406 represent the behavior of an electric motor without a controller that modifies the behavior of the electric motor. As can be seen, there are distinct differences.

Figure 9:
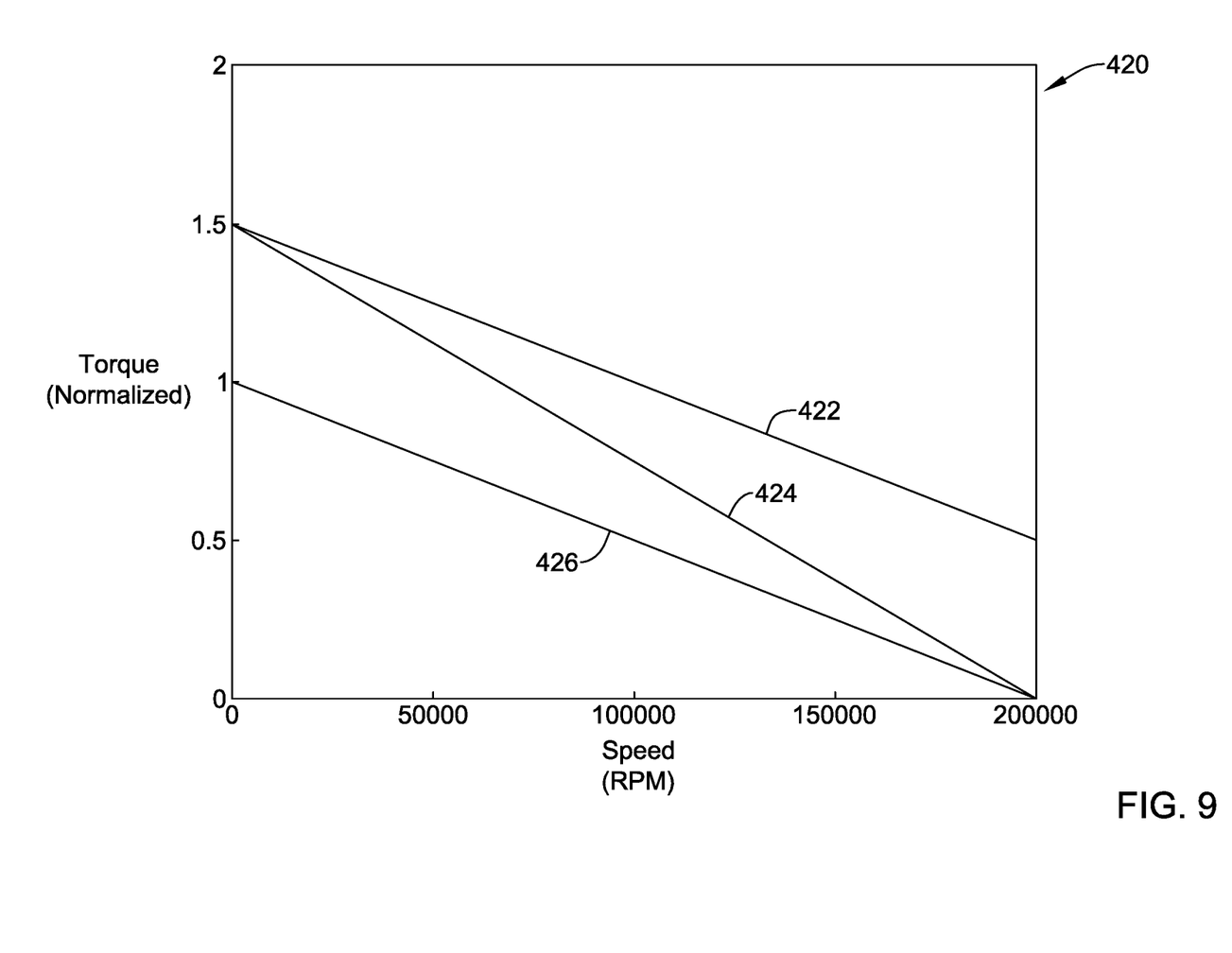

FIG. 9 is a representative plot 420 that shows the behavior when a PID (Proportional Integral Derivative) controller is used to regulate the operation of the electric motor. A curve 422 represents the working torque as measured at the electric motor. A curve 424 represents the working torque as measured at the burr (including frictional losses within the drive mechanism). A curve 426 represents the pneumatic working torque as measured at the burr. While the electric motor and the air turbine match relatively well at high speeds, they are increasing divergent as speed is reduced. One factor playing into this is the relatively higher frictional forces present within the electric system. This friction requires a large amount of torque to overcome at high speeds, which results in an excess of torque at low speeds. It will be appreciated that the relative friction may also vary from patient to patient and procedure to procedure.

Figure 10:
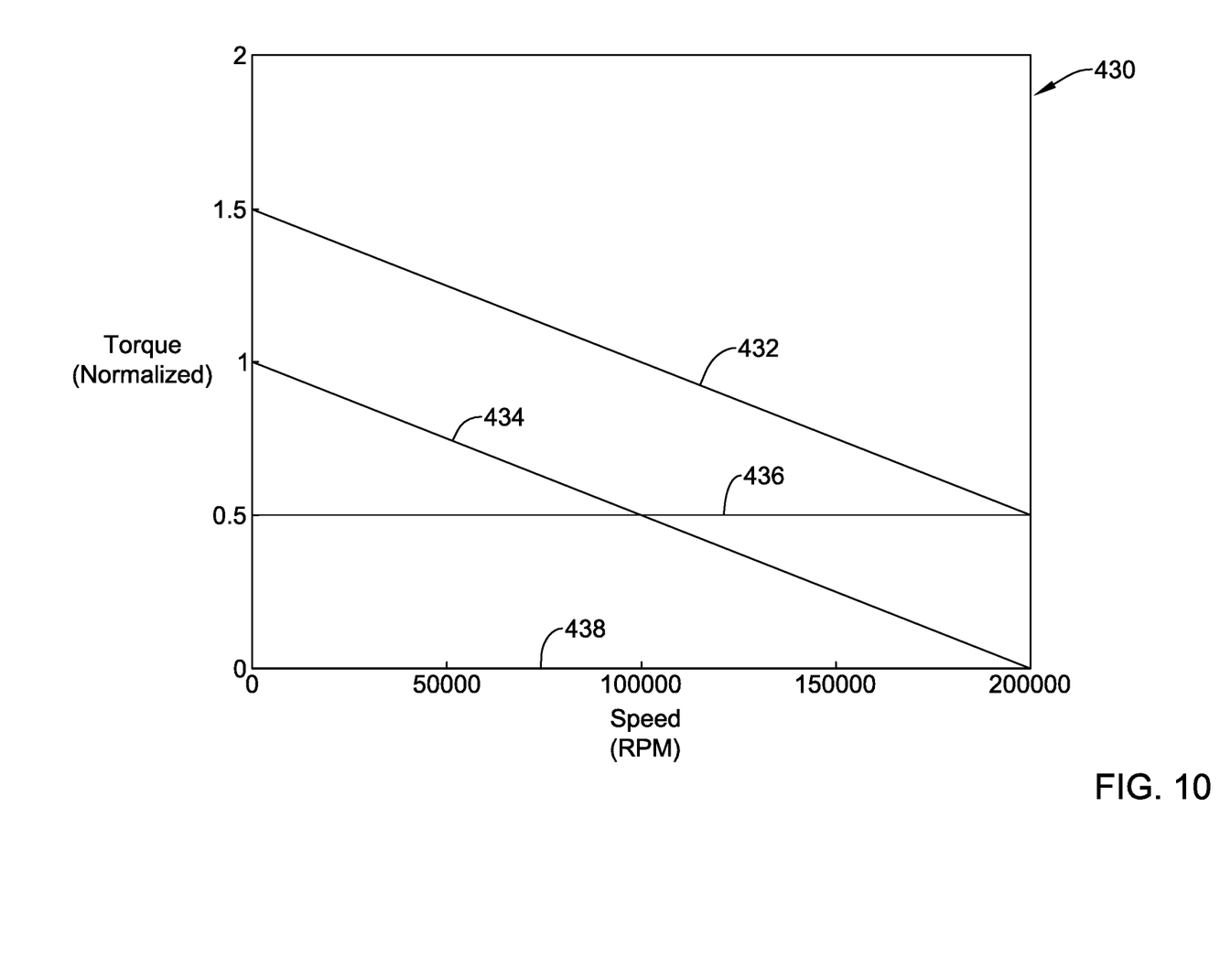

FIG. 10 shows a representative plot 430 that illustrates how much motor torque is driven by each of the components of a traditional PID controller. Line 432 illustrates a summation of the P, I and D components. Line 434 shows the P component contribution, line 436 shows the I component contribution and line 438 shows the D component contribution. While simply flattening the slope of the P component contribution may result in a slope of the overall torque curved (represented by the line 432) would more closely match that of an air turbine (as shown by the curve 408 in FIG. 8), simply reducing the P gain results in poor speed hold characteristics and excessive time to reach the target speed.

Figure 11:
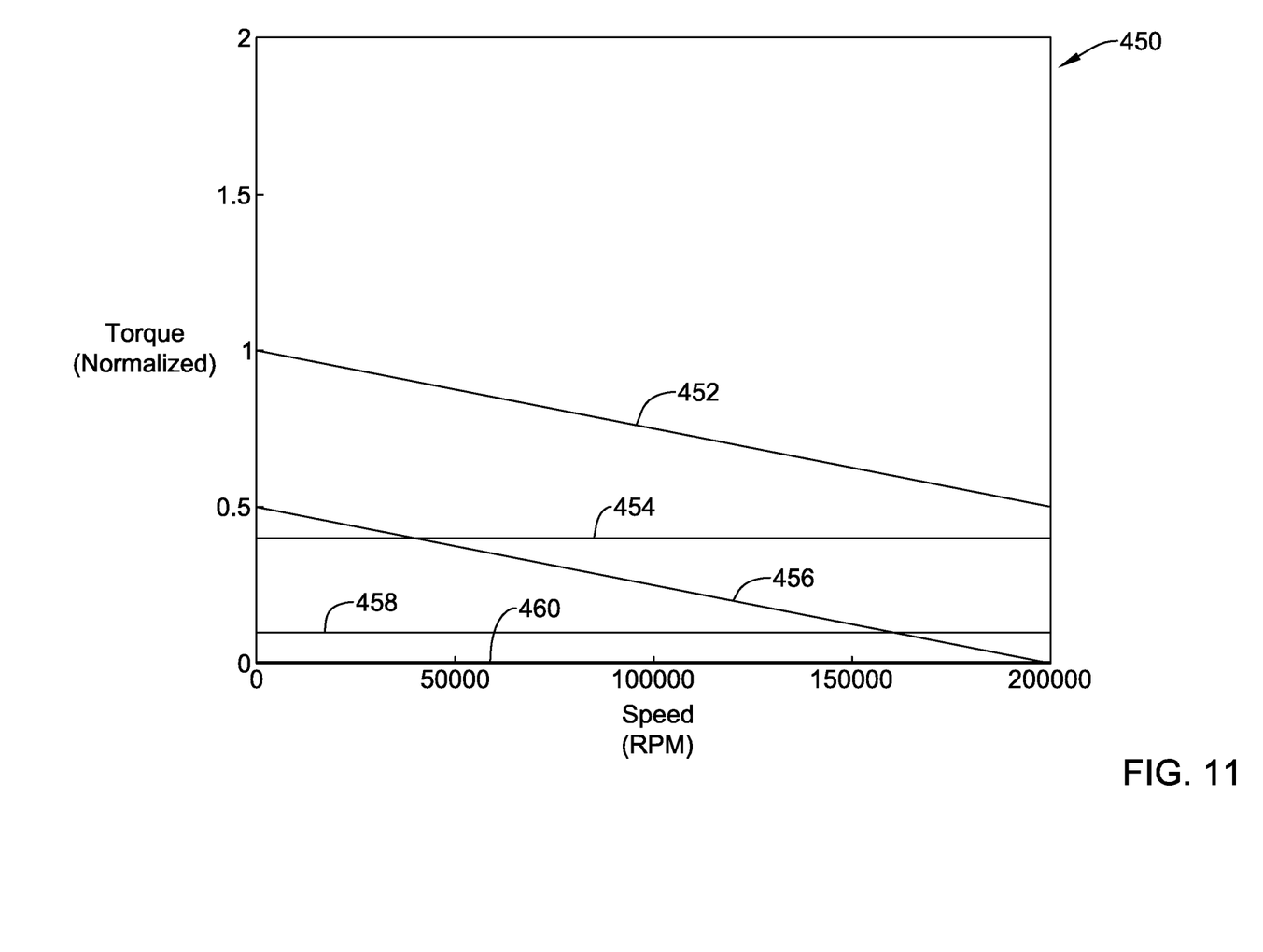

FIG. 11 shows a representative plot 450 that illustrates how much motor torque is driven by each of the components of a modified PID controller that includes a K offset value. In some cases, the value of K may be initially set to 0 (zero) in order to accelerate the electric system up to a speed reference. Once that speed reference is reached, the I gain may be reduced to a new constant value, the K value may be set to the sum of the instantaneous P and I terms, and then a new P gain is calculated.

Once the electric drive motor reaches the speed reference value, the controller may calculate a new value for P gain in accordance with equation (1) and a new value for the variable K offset term in accordance with equation (2):

$$P_{new} = \frac{T_{stall}(P_{old} + I_{old})}{\omega_{ref}}, \quad (1)$$

where
 $P_{new}$ is a new P gain value;
 $P_{old}$ is a previous P gain value;
 $O_{old}$ is a previous I gain value;
 $T_{stall}$ is a desired stall torque value; and
 $\omega_{ref}$ is the speed reference value.

$$K = P_{old}I_{old} \quad (2).$$

With reference to the plot 450, line 452 illustrates a summation of the P, I, D and K components. Line 454 shows the K contribution, line 456 shows the P component contribution, line 458 shows the I component contribution and line 460 shows the D component contribution. In comparing the line 452 (FIG. 11) to the line 432 (FIG. 10), it can be seen that the overall torque curve has been flattened, and thus is closer to that of an air turbine (as shown in FIG. 8 as the line 408).

In some cases, the controller may calculate a new value for P gain in accordance with equation (3) and a new value for the variable K offset term in accordance with equation (4):

$$K = P*e + I*\!\!\int e \quad (3)$$

$$P_{new} = \frac{i_{stall} - K}{\omega_{ref}}, \quad (4)$$

where
 $i_{stall}$ is the motor current that corresponds to a desired stall torque, which may be equal to the torque that an air turbine would produce at stall; and
 e is the error or difference between reference speed and the speed.

In some cases, these equations (3) and (4) are only used during transition from the conventional controller (used for acceleration) to the modified controller (used during the procedure). In some cases, this transition is only made once the value of the error e is small (less than 1 percent of the reference speed) in order to minimize any transient behavior.

Figure 12:
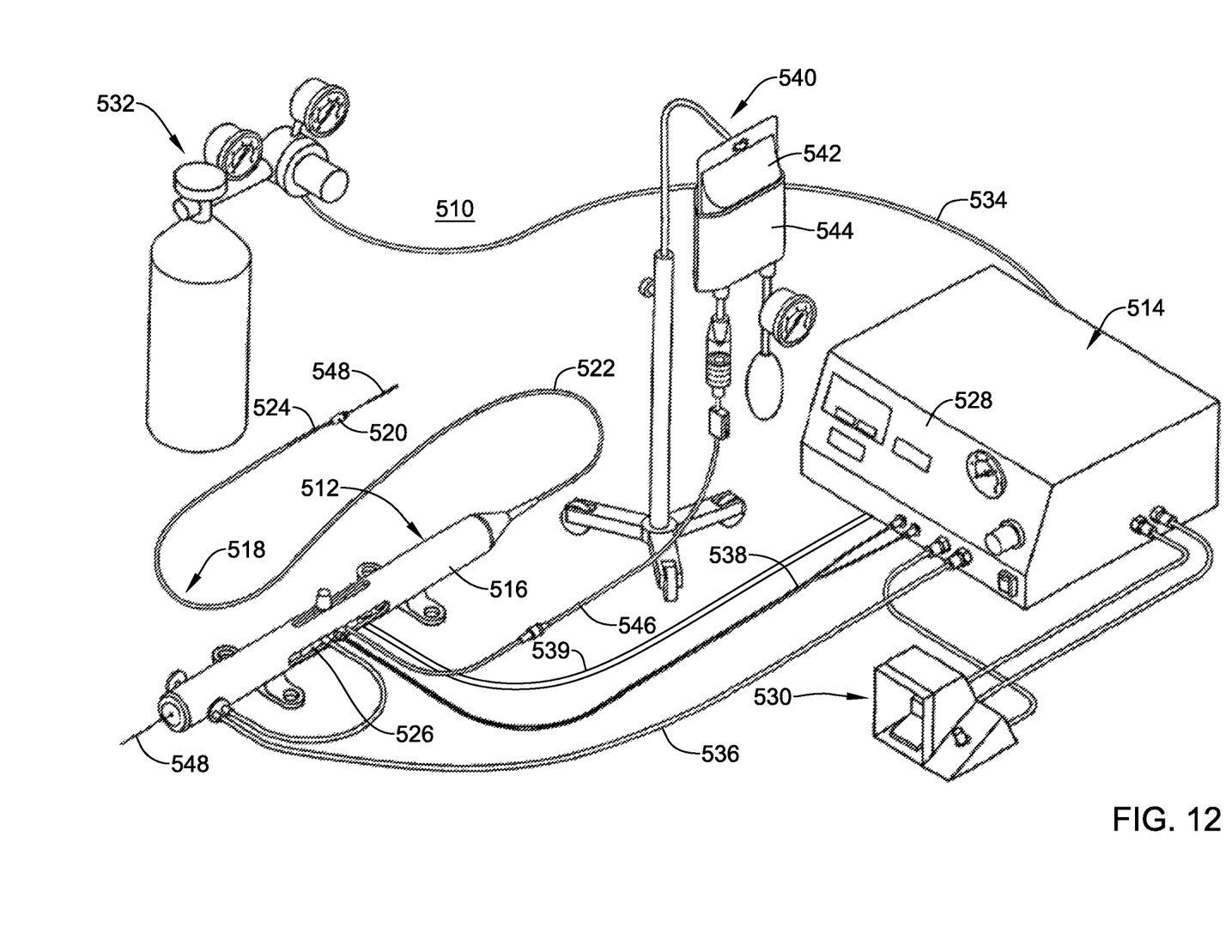
FIG. 12 is a schematic diagram of an example atherectomy system that may utilize the atherectomy control systems described with respect to FIGS. 1 through 6.

FIG. 12 shows an example rotational atherectomy system 510 with which the atherectomy systems 10, 20, 30, 40, 50 and 300 may be used. The rotational atherectomy system 510 may include a rotational atherectomy device 512 and a controller 514 for controlling the rotational atherectomy device 512. The rotational atherectomy device 512 may include a housing 516 and an elongate shaft 518 extending distally from the housing 516 to a cutting member 520 located at a distal end of the elongate shaft 518. The elongate shaft 518 may include a drive shaft 524 to provide rotational motion to the cutting member 520. In some instances, the elongate shaft 518 may include an outer tubular member 522 having a lumen extending therethrough and the drive shaft 524 may extend through the lumen of the outer tubular member 522. The drive shaft 524, which may be fixed to the cutting member 520, may be rotatable relative to the outer tubular member 522 to rotate the cutting member 520. In some instances the axial position of the cutting member 520 relative to the outer tubular member 522 may be adjusted by moving the drive shaft 524 longitudinally relative to the outer tubular member 522. For example, the atherectomy device 512 may include an advancer assembly 526 positioned in the housing 516, or otherwise provided with the housing 516, that is longitudinally movable relative to the housing 516. The outer tubular member 522 may be coupled to the housing 516 while the drive shaft 524 may be coupled to the advancer assembly 526. Accordingly, the drive shaft 524 (and thus the cutting member 520) may be longitudinally movable relative to the outer tubular member 522 by actuating the advancer assembly 526 relative to the housing 516.

The rotational atherectomy device 512 may include a prime mover (not shown) to provide rotational motion to the drive shaft 524 to rotate the cutting member 520. For example, in some instances the prime mover may be a fluid turbine within the housing 516, such as provided with the advancer assembly 526. In other instances, however, the prime mover may be an electrical motor, or the like. The controller 514 may be used to control the prime mover. For example, the user may provide power to the prime mover and/or control the speed of rotation of the drive shaft 524 via the controller 514. For example, the front panel 528 of the controller 514 may include a user interface including a power switch, speed control mechanism (e.g., a speed control knob and/or buttons), a display, and/or other features for controlling the rotational atherectomy device 512. In some instances, the rotational atherectomy system 510 may include a remote control device 530, such as a foot pedal, a hand control, or other mechanism which may be used to control the power and/or speed to the prime mover, for example.

In instances in which the prime mover is an electric motor, the electric motor may be coupled to the controller 514 via an electrical connection 539 to control the electric motor and/or provide electricity to the electric motor.

In some instances, the rotational atherectomy device 512 may include a speed sensor, such as an optical speed sensor, coupled to the controller 514 via a connector 538, such as a fiber optic connector to provide speed data to the controller 514. In other instances, an electronic sensor, such as a Hall Effect sensor, or other type of sensor may be used to sense the speed of the drive shaft 524 and cutting member 520. The speed data may be displayed, such as on the front panel 528 and/or the controller 514, and/or used to control the speed of the cutting member 520, such as maintaining a desired speed of the cutting member 520 during a medical procedure.

In some instances, the rotational atherectomy system 510 may be configured to infuse fluid through the elongate shaft 518 to the treatment site and/or aspirate fluid through the elongate shaft 518 from the treatment site. For example, the rotational atherectomy system 510 may include a fluid supply 540 for providing a flow of fluid through a lumen of the elongate shaft 518 to a treatment site. In some instances the fluid supply 540 may include a saline bag 542 which may be pressurized by a pressure cuff 544 to provide a pressurized fluid (e.g., saline) to the rotational atherectomy device 512 through a fluid supply line 546. In other instances, an infusion pump, such as a peristaltic pump, may be used to deliver pressurized fluid to the rotational atherectomy device 512. Additionally or alternatively, in some cases the rotational atherectomy system 510 may be configured to aspirate fluid from the treatment site. For example, the rotational atherectomy system 510 may include an aspiration pump, such as a peristaltic pump, to generate a vacuum to aspirate fluid through a lumen of the elongate shaft 518 to a fluid collection container (not shown), if desired.

In some instances, the elongate shaft 518 of the rotational atherectomy device 512 may be advanced over a guidewire 548 to a treatment site. For example, the drive shaft 524 may include a guidewire lumen through which the guidewire 548 may pass. Additionally or alternatively, the elongate shaft 518 may be advanced through a lumen of a guide catheter to a treatment site.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The scope of the disclosure is, of course, defined in the language in which the appended claims are expressed.

What is claimed is:

1. An atherectomy system, comprising:
    an electric drive mechanism adapted to rotatably actuate an atherectomy burr, the electric drive mechanism including:
        a drive cable coupled with the atherectomy burr; and
        an electric drive motor adapted to rotate the drive cable; and
    a controller adapted to regulate operation of the electric drive mechanism such that the electric drive mechanism emulates one or more performance characteristics of an air turbine including the torque versus speed performance characteristic of an air turbine.

2. The atherectomy system of claim 1, wherein the controller comprises:
    a reference block that is adapted to receive a speed signal and output a reference signal;
    a control block that is adapted to receive the reference signal from the reference block and generate a resulting control effort signal; and
    a drive circuit that is adapted to receive the control effort signal from the control block and regulate operation of the drive mechanism accordingly.

3. The atherectomy system of claim 2, wherein the control block of the controller utilizes a Proportional (P) gain, an Integral (I) gain and a Derivative (D) gain, modified to include a variable K offset value summed with a sum of the P gain, the I gain and the D gain.

4. The atherectomy system of claim 3, wherein the control block of the controller is configured to set an initial value for the variable K offset value equal to zero.

5. The atherectomy system of claim 3, wherein the control block of the controller is configured to calculate a new value for the variable K offset value when the electric drive motor reaches a speed reference value.

6. The atherectomy system of claim 5, wherein the control block of the controller is further configured, when the electric drive motor reaches the speed reference value, to calculate a new value for the P gain.

7. The atherectomy system of claim 6, wherein the control block of the controller is further configured, when the electric drive motor reaches the speed reference value, to calculate a new value for P gain in accordance with equation (1):

$$P_{new} = \frac{T_{stall}(P_{old} + I_{old})}{\omega_{ref}}, \qquad (1)$$

where
$P_{new}$ is a new P gain value;
$P_{old}$ is a previous P gain value;
$I_{old}$ is a previous I gain value;
$T_{stall}$ is a desired stall torque value; and
$\omega_{ref}$ is the speed reference value.

8. The atherectomy system of claim 7, wherein the control block of the controller is further configured, when the electric drive motor reaches the speed reference value, to calculate a new value for the variable K term in accordance with equation (2):

$$K = P_{old} + I_{old} \qquad (2).$$

9. The atherectomy system of claim 6, wherein the control block of the controller is further configured to calculate new values for the variable K term and the P term in accordance with equations (3) and (4):

$$K = P*e + I*\int e \qquad (3)$$

$$P_{new} = \frac{i_{stall} - K}{\omega_{ref}}, \qquad (4)$$

where
$i_{stall}$ is the motor current that corresponds to a desired stall torque; and
e is the error or difference between reference speed and the speed.

10. An atherectomy system, comprising:
a drive mechanism adapted to rotatably actuate an atherectomy burr, the electric drive mechanism including:
a drive cable coupled with the atherectomy burr; and
an electric drive motor adapted to rotate the drive cable; and
a control system adapted to regulate operation of the drive mechanism, the control system including:
a reference block for providing a speed reference value; and
a controller operably coupled to the reference block for receiving the speed reference value, the controller adapted to utilize the speed reference value, a Proportional (P) gain value, an Integral (I) gain value, a Derivative (D) gain value and a K offset value in determining an output signal for the drive mechanism;
wherein the controller is further adapted to initiate actuation of the drive mechanism using an initial value for the I gain value and a value of zero for the K offset value;
wherein the controller is further adapted to reduce the I gain value and calculate a non-zero value for the K offset value once a speed of the drive mechanism reaches the speed reference value; and
wherein the controller is further adapted to regulate operation of the electric drive mechanism such that the electric drive mechanism emulates the torque versus speed performance characteristic of an air turbine.

11. The atherectomy system of claim 10, wherein the controller is further adapted to also calculate a new P gain value once the speed of the drive mechanism reaches the speed reference value.

12. The atherectomy system of claim 11, wherein the new P gain value is related to a desired stall torque value or to the speed reference value.

13. An atherectomy system, comprising:
an electric drive motor adapted to actuate an atherectomy burr; and
a controller adapted to regulate operation of the electric drive motor, the controller adapted to utilize a speed reference value, a Proportional (P) gain value, an Integral (I) gain value, a Derivative (D) gain value and a K offset value in determining an output signal for the electric drive motor in order to emulate the torque versus speed performance characteristic of an air turbine.

14. The atherectomy system of claim 13, wherein the controller is configured to set an initial value for the variable K offset value equal to zero.

15. The atherectomy system of claim 13, wherein the controller is configured to calculate a new value for the variable K offset value when the electric drive motor reaches a speed reference value.

16. The atherectomy system of claim 15, wherein the controller is further configured, when the electric drive motor reaches the speed reference value, to calculate a new value for the P gain.

17. The atherectomy system of claim 15, wherein the controller is further configured to utilize estimated torque as a feedback value.

* * * * *